United States Patent
Takenaka (12)

(10) Patent No.: US 10,854,663 B2
(45) Date of Patent: Dec. 1, 2020

(54) RADIATION IMAGING APPARATUS AND RADIATION IMAGING SYSTEM

(71) Applicant: CANON KABUSHIKI KAISHA, Tokyo (JP)

(72) Inventor: Katsuro Takenaka, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 16/444,448

(22) Filed: Jun. 18, 2019

(65) Prior Publication Data

US 2019/0305033 A1 Oct. 3, 2019

Related U.S. Application Data

(63) Continuation of application No. PCT/JP2017/044189, filed on Dec. 8, 2017.

(30) Foreign Application Priority Data

Dec. 20, 2016 (JP) .................... 2016-247012

(51) Int. Cl.

| | |
|---|---|
| *G01T 1/17* | (2006.01) |
| *H01L 27/146* | (2006.01) |
| *H04N 5/32* | (2006.01) |
| *H04N 5/363* | (2011.01) |

(Continued)

(52) U.S. Cl.
CPC .......... *H01L 27/14663* (2013.01); *A61B 6/00* (2013.01); *G01T 1/17* (2013.01); *H04N 5/32* (2013.01); *H04N 5/363* (2013.01); *H04N 5/369* (2013.01)

(58) Field of Classification Search
CPC .... H01L 27/14663; H04N 5/32; H04N 5/363; H04N 5/369; A61B 6/00; G01T 1/17
See application file for complete search history.

(56) References Cited

U.S. PATENT DOCUMENTS

| | | | |
|---|---|---|---|
| 5,536,932 A | 7/1996 | Hack | |
| 2011/0134289 A1* | 6/2011 | Mochizuki | ............ H04N 5/361 348/246 |

(Continued)

FOREIGN PATENT DOCUMENTS

| | | |
|---|---|---|
| JP | 8-256292 A | 10/1996 |
| JP | 2012-129425 A | 7/2012 |
| JP | 2016-092587 A | 5/2016 |

*Primary Examiner* — Marcus H Taningco
(74) *Attorney, Agent, or Firm* — Canon U.S.A., Inc. IP Division

(57) ABSTRACT

A radiation imaging apparatus includes conversion elements which convert a radial ray into an electric signal, a signal line which reads electric signals obtained by the conversion elements, switch elements which are connected between the conversion elements and the signal line, and driving lines connected to control terminals of the switch elements. The first conversion element and the signal line are in a conductive state when a switch element connected to the first driving line is in an On state. The second conversion element and the signal line are in a conductive state when a switch element connected to the second driving line is in an On state. The third conversion element and the signal line are in a conductive state when a switch element connected to the first driving line and a switch element connected to the second driving line are in an On state.

11 Claims, 10 Drawing Sheets

(51) Int. Cl.
  *A61B 6/00* (2006.01)
  *H04N 5/369* (2011.01)

(56) References Cited

U.S. PATENT DOCUMENTS

| | | | |
|---|---|---|---|
| 2012/0126126 A1* | 5/2012 | Yokoyama | H01L 27/14676 250/366 |
| 2012/0154353 A1 | 6/2012 | Mochizuki | |
| 2013/0264488 A1* | 10/2013 | Sugawara | A61B 6/4233 250/394 |
| 2014/0241506 A1* | 8/2014 | Iwashita | G01T 1/16 378/91 |
| 2018/0006080 A1* | 1/2018 | Fujiyoshi | H01L 27/14612 |
| 2019/0110011 A1* | 4/2019 | Araki | H04N 5/3742 |

* cited by examiner

RADIATION IMAGING APPARATUS AND RADIATION IMAGING SYSTEM

CROSS-REFERENCE TO RELATED APPLICATIONS

This application is a Continuation of International Patent Application No. PCT/JP2017/044189, filed Dec. 8, 2017, which claims the benefit of Japanese Patent Application No. 2016-247012, filed Dec. 20, 2016, both of which are hereby incorporated by reference herein in their entirety.

TECHNICAL FIELD

The present invention relates to a radiation imaging apparatus and a radiation imaging system.

BACKGROUND ART

A radiation imaging apparatus which electrically captures an optical image formed by radiation includes a driving circuit which drives a pixel array and a reading circuit which reads electric signals from the pixel array as peripheral circuits disposed around the pixel array. According to a radiation imaging apparatus disclosed in PTL 1, a multiplexer connected between a pixel array and a reading circuit switches a plurality of signal lines from one to another so that signals are read to the reading circuit. In this way, a configuration of the reading circuit is simplified.

CITATION LIST

Patent Literature

PTL 1 Japanese Patent Laid-Open No. 8-256292

A kTC noise is generated in a signal line due to parasitic capacitance generated between the signal line and a gate line, a bias line, or a transistor. Correlated double sampling is performed to remove the kTC noise. Specifically, a kTC noise generated after a potential of a signal line is reset is sampled and the noise is subtracted from a signal read from a pixel array so that the kTC noise is removed. According to the configuration disclosed in PTL 1, the signal lines connected to the reading circuit are switched from one to another by the multiplexer, and therefore, when a signal line which has not been selected is to be read, a kTC noise in the signal line may not be removed.

SUMMARY OF INVENTION

An object of the present invention is to provide a technique of enabling removal of noise generated in a signal line and reducing the number of contacts between a pixel array and peripheral circuits. To address the problems described above, there is provided a radiation imaging apparatus including a plurality of conversion elements configured to convert a radial ray into an electric signal, a signal line configured to read electric signals obtained by the plurality of conversion elements, a plurality of switch elements configured to be connected between the plurality of conversion elements and the signal line, and a plurality of driving lines configured to be connected to control terminals of the plurality of switch elements. The plurality of conversion elements include a first conversion element, a second conversion element, and a third conversion element. The plurality of driving lines include a first driving line and a second driving line. The first conversion element and the signal line are in a conductive state when a switch element connected to the first driving line is in an On state. The second conversion element and the signal line are in a conductive state when a switch element connected to the second driving line is in an On state. The third conversion element and the signal line are in a conductive state when a switch element connected to the first driving line and a switch element connected to the second driving line are in an On state.

Further features of the present invention will become apparent from the following description of exemplary embodiments with reference to the attached drawings.

DESCRIPTION OF EMBODIMENTS

Figure 1:
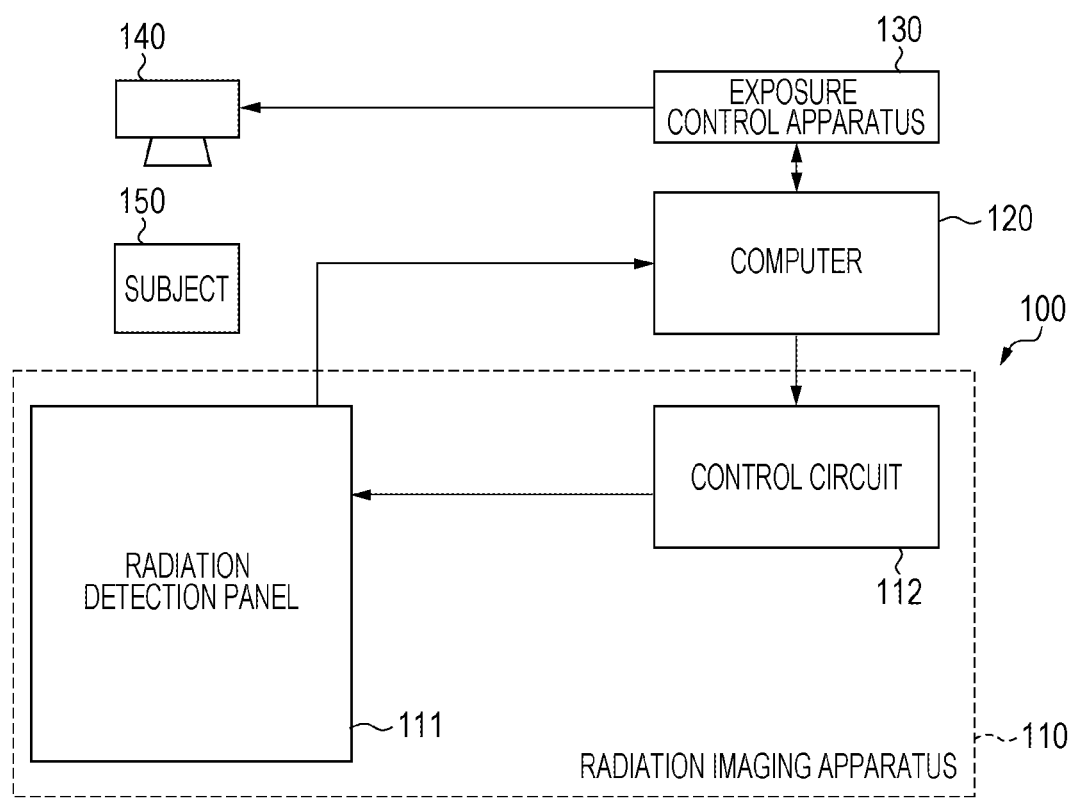
FIG. 1 is a diagram illustrating an example of a configuration of a radiation imaging system according to a first embodiment of the present invention.

Embodiments of the present invention will be described hereinafter with reference to the accompanying drawings. The same components are denoted by the same reference numerals and redundant descriptions are omitted in the embodiments. Furthermore, the embodiments may be appropriately modified and combined with each other.

First Embodiment

FIG. 1 is a diagram illustrating an example of a configuration of a radiation imaging system 100 according to a first embodiment of the present invention. The radiation imaging system 100 electrically captures an optical image formed by radiation so as to obtain an electrical radiation image. Although a typical example of the radiation is an X ray, the radiation may be an α ray, a β ray, a γ ray, or the like. The radiation imaging system 100 includes a radiation imaging apparatus 110, a computer 120, an exposure control apparatus 130, and a radiation source 140.

The radiation source 140 starts emission of a radial ray in accordance with an exposure instruction (a radiation instruction) issued by the exposure control apparatus 130. The radial ray emitted from the radiation source 140 is incident on the radiation imaging apparatus 110 through a subject 150. The radiation source 140 also stops the emission of a radial ray in accordance with a stop instruction issued by the exposure control apparatus 130.

The radiation imaging apparatus 110 includes a radiation detection panel 111 and a control circuit 112. The radiation detection panel 111 generates radiation image data corresponding to a radial ray which is incident on the radiation imaging apparatus 110 and transmits the radiation image data to the computer 120. The radiation image data is data on a radiation image. The control circuit 112 controls operation of the radiation detection panel 111. For example, the control circuit 112 generates a stop signal so as to stop emission of a radial ray from the radiation source 140 based on a signal obtained from the radiation detection panel 111. The stop signal is supplied to the exposure control apparatus 130. The exposure control apparatus 130 transmits a stop instruction to the radiation source 140 in response to the stop signal. The control circuit 112 may be constituted by a dedicated circuit, such as a programmable logic device (PLD) including a field programmable gate array (FPGA) or an application specific integrated circuit (ASIC). Alternatively, the control circuit 112 may be constituted by a combination between a general processing circuit, such as a processor, and a storage circuit, such as a memory. In this case, functions of the control circuit 112 may be realized when the general processing circuit executes a program stored in the storage circuit.

The computer 120 includes a controller which controls the radiation imaging apparatus 110 and the exposure control apparatus 130, a reception unit which receives radiation image data from the radiation imaging apparatus 110, and a signal processing unit which processes a signal (radiation image data) obtained by the radiation imaging apparatus 110. Each of the controller, the reception unit, and the signal processing unit may be configured by a dedicated circuit or a combination of a general processing circuit and a storage circuit similarly to the control circuit 112. The exposure control apparatus 130 has an exposure switch, for example. When the exposure switch is turned on, the exposure control apparatus 130 transmits an exposure instruction to the radiation source 140 and a start notification indicating start of emission of a radial ray to the computer 120. The computer 120 which has received the start notification notifies the control circuit 112 in the radiation imaging apparatus 110 of the start of emission of a radial ray in response to the start notification.

Figure 2:
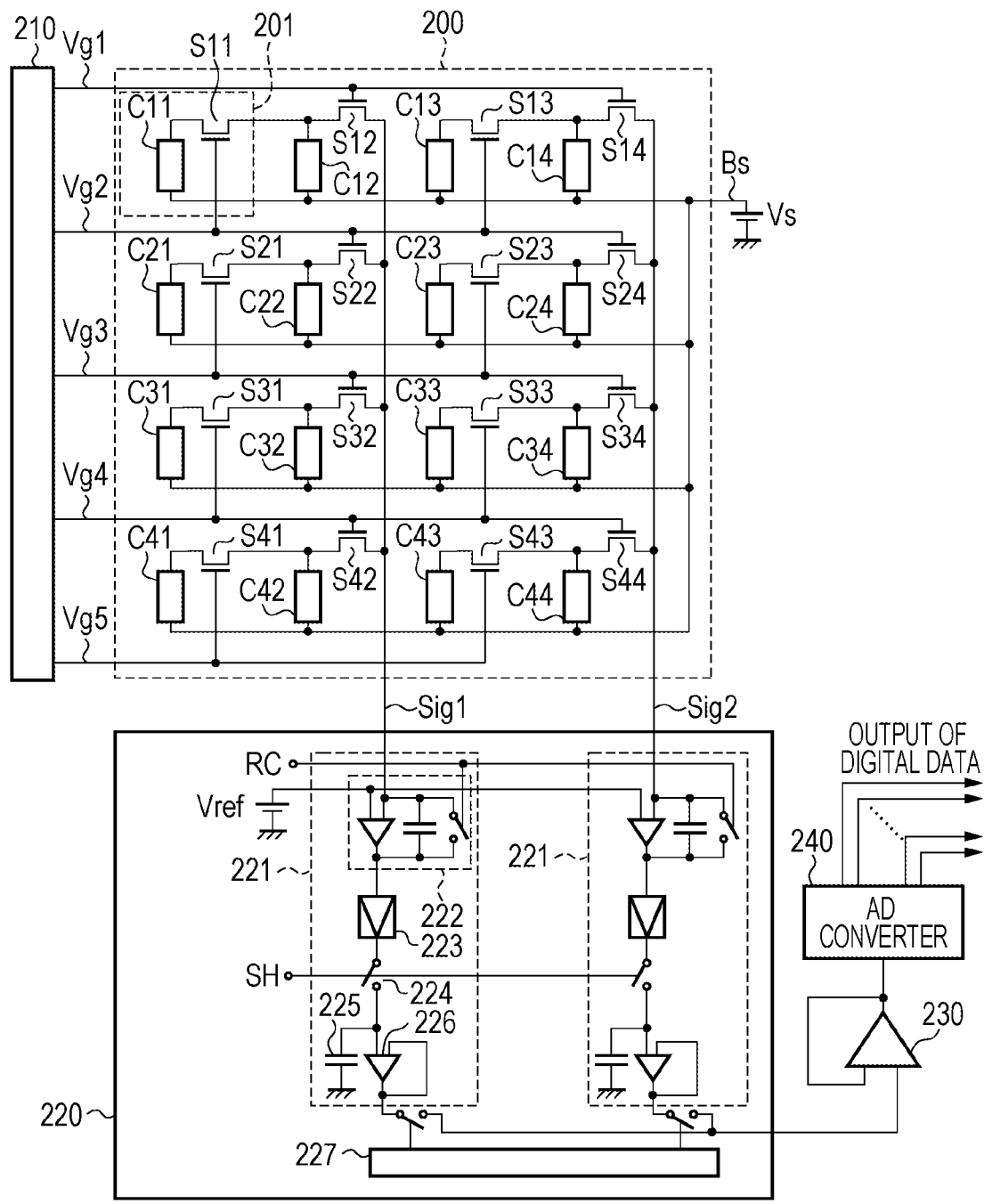
FIG. 2 is a diagram illustrating an example of a configuration of a radiation imaging apparatus according to the first embodiment of the present invention.

FIG. 2 is a diagram illustrating an example of a configuration of the radiation detection panel 111. The radiation detection panel 111 includes a pixel array 200, a driving circuit 210, a reading circuit 220, a buffer circuit 230, and an AD converter 240, for example. The driving circuit 210 and the reading circuit 220 function as peripheral circuits of the pixel array 200. The pixel array 200 includes, for example, a plurality of pixels 201 arranged in an array, a plurality of driving lines Vg1 to Vg5, a plurality of signal lines Sig1 and Sig2, and a bias line Bs. In FIG. 2, for a description, the pixel array 200 includes the pixels 201 in a matrix of 4 rows by 4 columns. However, a larger number of pixels 201 may be arranged in practice. For example, the radiation detection panel 111 has a size of 17 inches and has pixels 201 in a matrix of approximately 3000 rows by approximately 3000 columns. Each of the pixels 201 includes a conversion element and a switch element.

The pixel array 200 includes a plurality of conversion elements C11 to C44 and a plurality of switch elements S11 to S44. In a description below, the conversion elements C11 to C44 are collectively referred to as a conversion element C. A description about the conversion element C is employed in each of the conversion elements C11 to C44. Similarly, the switch elements S11 to S44, the driving lines Vg1 to Vg5, and the signal lines Sig1 and Sig2 are collectively referred to as a switch element S, a driving line Vg, and a signal line Sig, respectively. The rows of the pixel array 200 are referred to as first to fourth rows from an upper side of FIG. 2, and the columns of the pixel array 200 are referred to as first to fourth columns from a left side of FIG. 2. Each of the pixels 201 is configured by a combination of a single conversion element C and a single switch element S. For example, the pixel 201 in the first row and the second column is configured by a combination of a conversion element C12 and a switch element S12.

In each of the pixels 201, the conversion element C converts an incident radial ray to an electric signal (a charge, for example), the switch element S is connected between the conversion element C and a signal line Sig for the conversion element C. For example, switch elements S11, S12, S21, and S22 are connected between a plurality of conversion elements C11, C12, C21, and C22 and the signal line Sig1. When the switch element S is turned on, the conversion element C and the signal line Sig are brought into a conductive state, and an electric signal obtained by the conversion element C (a charge accumulated in the conversion element C, for example) is transferred to the signal line Sig. The conversion element C may be an MIS-type photodiode which mainly includes an amorphous silicon as material and which is disposed on an insulation substrate, such as a glass substrate. Alternatively, the conversion element C may be a PIN type photodiode. The conversion element C may be configured as a direct type which directly converts a radial ray into a charge or an indirect type which converts a radial ray into light, and thereafter, detects the light. As the indirect type, the scintillator may be shared by the plurality of pixels 201.

The switch element S is constituted by a transistor having a control terminal (a gate) and two main terminals (a source and a drain), such as a thin film transistor (TFT), for example. The conversion element C includes two main electrodes. One of the main electrodes of the conversion element C is connected to one of the two main terminals of the switch element S, and the other of the main electrodes of the conversion element C is connected to a bias power source Vs through the common bias line Bs. The bias power source Vs generates a bias voltage.

Control terminals of switch elements S of the pixels 201 in the first row and even-numbered columns are connected to the driving line Vg1, and control terminals of switch elements S of the pixels 201 in the first row and odd-numbered columns are connected to the driving line Vg2. Control terminals of switch elements S of the pixels 201 in the second row and even-numbered columns are connected to the driving line Vg2, and control terminals of switch elements S of the pixels 201 in the second row and odd-numbered columns are connected to the driving line Vg3. The same is true of the third and fourth rows. Furthermore, one of main terminals of each of switch elements S of the pixels 201 in the first column is connected to a conversion element C in the same pixel 201, and the other of the main terminals is connected to a conversion element C of the pixel 201 in the second column. Specifically, the switch element S of the pixel 201 in the first column is connected to the signal line Sig through the switch element S of the pixel 201 in the second column. One of main terminals of each of switch elements S of the pixels 201 in the second column is connected to the conversion element C in the same pixel 201, and the other of the main terminals is connected to the signal line Sig. Specifically, the switch elements S of the pixels 201 in the second columns are connected between the conversion elements C in the same pixels and the signal line Sig. The same is true of the third and fourth columns.

For example, the switch element S12 is connected between the conversion element C12 and the signal line Sig1. The switch elements S11 and S12 are connected in series between the conversion element C11 and the signal line Sig1. The switch element S11 is connected to the signal line Sig1 through the switch element S12. The switch element S22 is connected between the conversion element C22 and the signal line Sig1. The conversion elements C12 and C22 are arranged in a direction in which the signal line Sig1 extends. The conversion elements C11 and C12 are arranged in a direction in which the driving line Vg1 extends.

In this connection form, the number of signal lines Sig is only a half of the number of columns in the pixel array 200. Furthermore, the number of driving lines Vg is larger by one than the number of rows in the pixel array 200. Therefore, when compared with a radiation detection panel which has driving lines for individual pixel rows and signal lines for individual pixel columns, the number of contacts between the pixel array 200 and the peripheral circuits (the driving circuit 210 and the reading circuit 220) (the total number of the driving lines Vg and the signal lines Sig) is reduced. Consequently, configurations of the peripheral circuits are simplified.

The three conversion elements C11, C12, and C22 are focused on, and a condition for a conductive state between the signal line Sig and the three conversion elements C11, C12, and C22 will be described. The conversion element C12 and the signal line Sig1 are in a conductive state when the switch element S12 connected to the driving line Vg1 is in an On state and are in a non-conductive state when the switch element S12 connected to the driving line Vg1 is in an Off state. The conversion element C22 and the signal line Sig1 are in a conductive state when the switch element S22 connected to the driving line Vg2 is in an On state and are in a non-conductive state when the switch element S22 connected to the driving line Vg2 is in an Off state. The conversion element C11 and the signal line Sig1 are in a conductive state when the switch element S12 connected to the driving line Vg1 and the switch element S11 connected to the driving line Vg2 are in an On state and are in a non-conductive state when at least one of the switch element S12 and the switch element S11 is in an Off state.

The driving circuit 210 supplies a driving signal to the control terminals of the switch elements S of the individual pixels 201 through the driving line Vg in accordance with a control signal supplied from the control circuit 112. The control signal includes an On signal (a voltage of a high level in a description below) which causes the switch element S to be turned on and an Off signal (a voltage of a low level in the description below) which causes the switch element S to be turned off. The driving circuit 210 includes a shift register, for example, and the sift register performs a shift operation in accordance with a control signal supplied from the control circuit 112 (a clock signal, for example). An example of operation of the driving circuit 210 will be described hereinafter.

The reading circuit 220 amplifies and reads an electric signal which is obtained by the conversion element C and supplied to the signal line Sig. The reading circuit 220 includes amplification circuits 221 which correspond to the signal lines Sig. Since the pixel array 200 includes the two signal lines Sig in the example of FIG. 2, the reading circuit 220 includes the two amplification circuits 221. Each of column amplification units 221 includes an integrating amplifier 222, a variable amplifier 223, a switch element 224, a capacitor 225, and a buffer circuit 226. The switch element 224 and the capacitor 225 form a sample-and-hold circuit. The integrating amplifier 222 includes an operational amplifier and includes an integrating capacitor and a reset switch which are connected in parallel between an inverting input terminal and an output terminal of the operational amplifier. The operational amplifier has a non-inverting input terminal which receives a reference voltage supplied from a reference power source Vref. When the reset switch is turned on in response to a control signal RC (a reset pulse) supplied from the control circuit 112, the integrating capacitor is reset and a potential of the signal line Sig is reset to a reference potential.

The variable amplifier 223 amplifies a signal supplied from the integrating amplifier 222 in a preset amplification factor. The sample-and-hold circuit samples and holds a signal supplied from the variable amplifier 223. The switch element 224 included in the sample-and-hold circuit is turned on or off by a control signal SH supplied from the control circuit 112. The buffer circuit 226 buffers (performs impedance conversion on) a signal supplied from the sample-and-hold circuit and outputs a resultant signal.

The reading circuit 220 further includes a multiplexer 227 which selects and outputs signals supplied from the plurality of amplification circuits 221 in predetermined order. The multiplexer 227 includes a shift register, for example, and the sift register performs a shift operation in accordance with a control signal supplied from the control circuit 112 (a clock signal, for example). In this shift operation, one of the signals supplied from the plurality of amplification circuits 221 is selected.

The buffer circuit 230 performs buffering (impedance conversion) on a signal output from the multiplexer 227. The AD converter 240 converts an analog signal output from the buffer circuit 230 into a digital signal. An output of the AD converter 240, that is, radiation image data, is transmitted to the computer 120.

Figure 3:
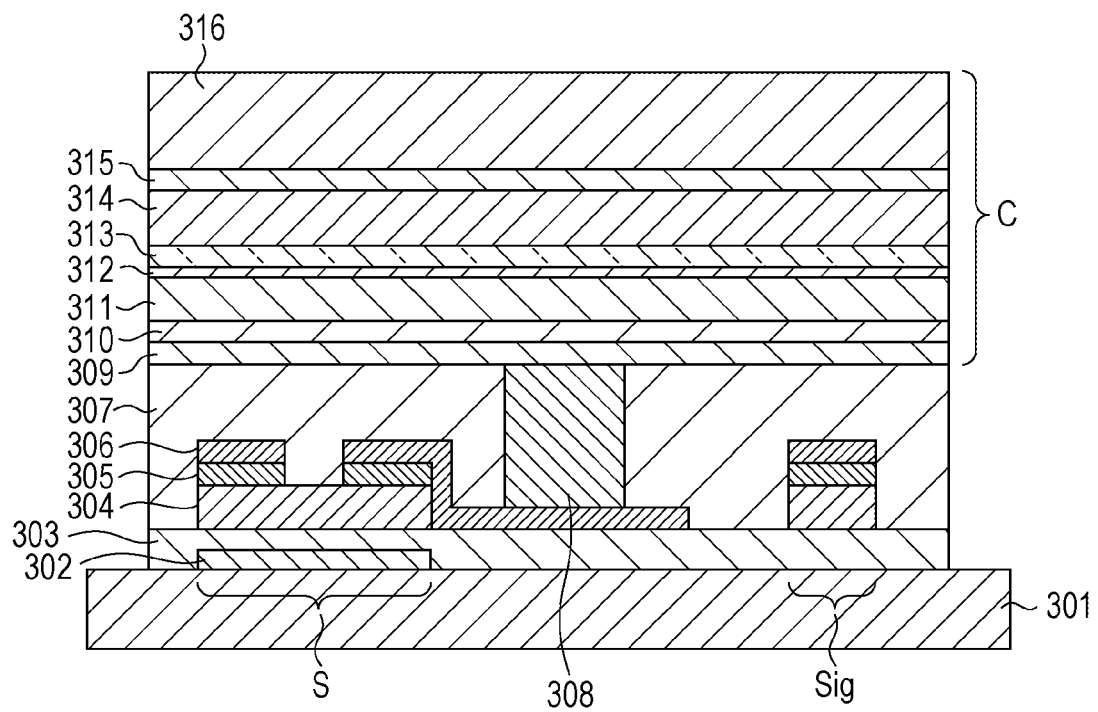
FIG. 3 is a diagram illustrating an example of a configuration of a cross section of a pixel according to the first embodiment of the present invention.

FIG. 3 is a diagram schematically illustrating an example of a cross-sectional configuration of one of the pixels 201. The pixel 201 is formed on an insulation substrate 301, such as a glass substrate. The pixel 201 includes a conductive layer 302, an insulation layer 303, a semiconductor layer 304, an impurity semiconductor layer 305, and a conductive layer 306 on the insulation substrate 301. The conductive layer 302 constitutes a gate of the transistor (a TFT, for example) included in the switch element S. The insulation layer 303 is disposed so as to cover the conductive layer 302. The semiconductor layer 304 is disposed on a portion corresponding to the gate of the conductive layer 302 through the insulation layer 303. The impurity semiconductor layer 305 is disposed on the semiconductor layer 304 so as to form the two main terminals (the source and the drain) of the transistor included in the switch element S. The conductive layer 306 constitutes wiring patterns connected to the individual two main terminals (the source and the drain) of the transistor included in the switch element S. A portion of the conductive layer 306 forms the signal line Sig, and the other forms a wiring pattern for connection between the conversion element C and the switch element S.

The pixel 201 further includes an interlayer insulation film 307 which covers the insulation layer 303 and the conductive layer 306. The interlayer insulation film 307 has a contact plug 308 for the connection to the conductive layer 306 (the switch element S). The pixel 201 further includes a conductive layer 309, an insulation layer 310, a semiconductor layer 311, an impurity semiconductor layer 312, a conductive layer 313, a protection layer 314, a contact layer 315, and a scintillator layer 316 on the interlayer insulation film 307 in this order. These layers constitute an indirect-type conversion element C. The conductive layers 309 and 313 constitute lower and upper electrodes, respectively, of a photoelectric conversion element included in the conversion element C. The conductive layer 313 is constituted by a transparent material, for example. The conductive layer 309, the insulation layer 310, the semiconductor layer 311, the impurity semiconductor layer 312, and the conductive layer 313 constitute an MIS sensor serving as a photoelectric conversion element. The impurity semiconductor layer 312 is formed as an n-type impurity semiconductor layer, for example. The scintillator layer 316 is formed of a material of a gadolinium system or a material of cesium iodide (CsI) and converts a radial ray into light.

Instead of the example described above, the conversion element C may be a direct-type conversion element which directly converts an incident radial ray into an electric signal (charge). Examples of the direct-type conversion element C include a conversion element having amorphous selenium, gallium arsenic, gallium phosphide, lead iodide, mercuric iodide, CdTe, CdZnTe, or the like as a main material, for example. The conversion element C is not limited to an MIS type and may be a pn type photodiode or a PIN type photodiode, for example.

In the example illustrated in FIG. 3, each of the signal lines Sig overlaps with a portion of the conversion element C in orthographic projection (a plan view) relative to a plane on which the pixel array 200 is formed. This configuration is advantageous in that an area of the conversion element C of each of the pixels 201 is large whereas this configuration is disadvantageous in that a capacitance coupling between the signal line Sig and the conversion element C is large. In a case where a radial ray is incident on the conversion element C, charge is accumulated in the conversion element C, and a potential of the conductive layer 309 (a lower electrode) is changed, a potential of the signal line Sig is also changed due to the capacitance coupling between the signal line Sig and the conversion element C.

Figure 4:
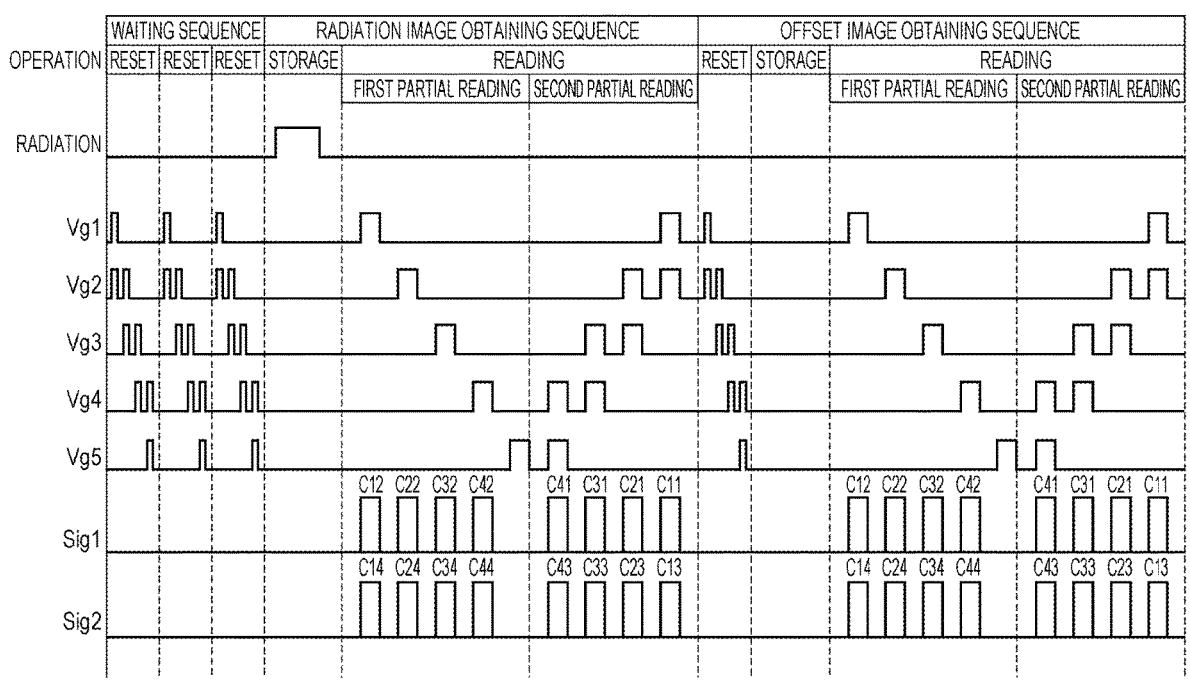
FIG. 4 is a diagram illustrating an example of an operation of the radiation imaging system according to the first embodiment of the present invention.

FIG. 4 is a diagram illustrating an example of operation of the radiation imaging system 100. The operation of the radiation imaging system 100 is controlled by the computer 120. Operation of the radiation imaging apparatus 110 is controlled by the control circuit 112 under control of the computer 120. The operation illustrated in FIG. 4 is started in response to an instruction of a user of the radiation imaging system 100, for example.

A term "operation" in FIG. 4 indicates the operation of the radiation imaging system 100. The operation of the radiation imaging system 100 includes a waiting sequence, a radiation image obtaining sequence, and an offset image obtaining sequence. The waiting sequence is a series of operations performed while start of emission of a radial ray is waited. The radiation image obtaining sequence is a series of operations of obtaining a radiation image. The offset image obtaining sequence is a series of operations of obtaining an offset image. The offset image is formed by signals obtained from the individual pixels 201 in a state in which a radial ray is not emitted to the radiation imaging apparatus 110. A term "radiation" in FIG. 4 indicates presence or absence of emission of a radial ray. A low level indicates that a radial ray is not emitted and a high level indicates that a radial ray is emitted. In FIG. 4, "Vg1" to "Vg5" indicate levels of driving signals supplied to the individual driving lines Vg1 to Vg5 from the driving circuit 210. A switch element S connected to the driving line Vg to which a driving signal of a low level (an Off signal) is supplied is in an Off state, and a switch element S connected to the driving line Vg to which a driving signal of a high level (an On signal) is supplied is in an On state. In FIG. 4, "Sig1" and "Sig2" indicate whether signals are being read through the corresponding signal lines Sig1 and Sig2 and indicate conversion elements C of a reading target. A low level indicates that a signal has not been read and a high level indicates that a signal has been read. Furthermore, in a case of the high level, reference numerals of the conversion elements C of the reading target are described.

In the waiting sequence, the radiation imaging apparatus 110 repeatedly performs a resetting operation. The resetting operation is an operation of resetting dark charge accumulated in the conversion elements C of the individual pixels 201. The dark charge is generated although a radial ray is not incident on the conversion element C. An operation of successively resetting the conversion elements C of the pixels 201 in the first row to the pixels 201 in the last row (the fourth row) is referred to as a single resetting operation. The radiation imaging apparatus 110 repeatedly performs this resetting operation. During the resetting operation, the control circuit 112 supplies a reset pulse of an active level to the reset switch of the integrating amplifier 222. By this, the signal line Sig is reset to a reference potential. By the single resetting operation, the driving circuit 210 supplies an On signal to the driving lines Vg1 and Vg2 so as to reset the pixels 201 in the first row. By this, the conversion element C11 and the signal line Sig1 are brought into a conductive state and the conversion element C12 and the signal line Sig1 are brought into a conductive state. The same is true of the conversion elements C13 and C14. Subsequently, the driving circuit 210 supplies an On signal to the driving lines Vg2 and Vg3 so as to reset the pixels 201 in the second row. Thereafter, the driving circuit 210 similarly performs the resetting until the pixels 201 in the fourth row are processed.

The control circuit 112 recognizes that the radiation source 140 starts emission of a radial ray based on a start notification supplied from the exposure control apparatus 130 through the computer 120, for example, and the waiting sequence is shifted to the radiation image obtaining sequence. Alternatively, the radiation imaging apparatus 110 may include a detection circuit which detects current which is supplied in the bias line Bs or the signal line Sig of the pixel array 200 and recognize that the radiation source 140 starts emission of a radial ray based on an output of the detection circuit.

The radiation image obtaining sequence includes an accumulating operation and a reading operation. In the accumulating operation, the driving circuit 210 supplies an Off signal to the individual driving line Vg1 to Vg5 for a predetermined period of time. By this, charge corresponding to radial rays which are incident on the individual conversion elements C is accumulated in the conversion elements C. Thereafter, in the reading operation, the control circuit 112 reads charge (an electric signal) accumulated in the conversion elements C. In this embodiment, the reading operation is divided into two partial reading operations. Specifically, the control circuit 112 reads charge from the conversion elements C of the pixels 201 in the even-numbered columns in the first partial reading operation and reads charge from the conversion elements C of the pixels 201 in the odd-numbered columns in the second partial reading operation.

Hereinafter, the reading operation will be described in detail. Although charge read through the signal line Sig1 is mainly described, the same is true of charge read through the signal line Sig2. First, the driving circuit 210 supplies an On signal only to the driving line Vg1. By this, the switch element S12 is turned on and the conversion element C12 and the signal line Sig1 are brought into a conductive state, and therefore, charge obtained by the conversion element C12 is read to the signal line Sig1. On the other hand, since an Off signal is supplied to the driving line Vg2, the switch element S11 remains in the Off state and the conversion element C11 and the signal line Sig1 are in a non-conductive state. Accordingly, the charge obtained by the conversion element C11 is not read to the signal line Sig1 at this time point.

After the charge obtained by the conversion element C12 is read, the driving circuit 210 supplies an On signal only to the driving line Vg2. By this, the switch element S22 is turned on and the conversion element C22 and the signal line Sig1 are brought into a conductive state, and therefore, charge obtained by the conversion element C22 is read to the signal line Sig1. Furthermore, the switch element S11 is also turned on, and therefore, the conversion element C11 and the conversion element C12 are brought into a conductive state through the switch element S11. Therefore, a portion of the charge obtained by the conversion element C11 is transferred to the conversion element C12. On the other hand, since an Off signal is supplied to the driving line Vg1, the switch element S12 is in an Off state and the conversion element C11 and the signal line Sig1 are in a non-conductive state. Accordingly, the charge obtained by the conversion element C11 is not read to the signal line Sig1 at this time point. After the charge obtained by the conversion element C22 is read, the driving circuit 210 sequentially supplies an On signal to the driving lines Vg3 to Vg5. By this, charge obtained by the conversion elements C32 and C42 is similarly read to the signal line Sig1. The first partial reading operation is thus terminated.

Subsequently, the control circuit 112 performs the second partial reading operation. In the second partial reading operation, unlike the first partial reading operation, charge is successively read from the pixels 201 in the last row (the fourth row) to the pixels 201 in the first row. First, the driving circuit 210 supplies an On signal to the driving lines Vg4 and Vg5. By this, switch elements S41 and S42 are turned on and a conversion element C42 and the signal line Sig1 are brought into a conductive state, and therefore, charge obtained by the conversion element C41 is read to the signal line Sig1. Although a portion of the charge obtained by the conversion element C41 is transferred to the conversion element C42 in the first partial reading operation, the partial charge is also read to the signal line Sig1 in addition to the charge obtained by the conversion element C41 since the conversion element C42 and the signal line Sig1 are in a conductive state. Furthermore, the charge obtained by the conversion element C42 has been read by the first partial reading operation, and therefore, only the charge obtained by the conversion element C41 is read. Since an On signal has been supplied to the driving line Vg4, the switch element S31 is also turned on. However, since the switch element S32 is in an Off state, charge obtained by the conversion element C31 is not read to the signal line Sig1.

After the charge obtained by the conversion element C41 is read, the driving circuit 210 successively supplies an On signal to the driving lines Vg4 to Vg1 in a unit of two lines. Accordingly, the charge obtained by the conversion elements C31, C21, and C11 is similarly read to the signal line Sig1. The second partial reading operation is thus terminated.

The radiation imaging apparatus 110 transmits the charge of the conversion elements C obtained in the radiation image obtaining sequence as a digital signal to the computer 120 through the multiplexer 227, the buffer circuit 230, and the AD converter 240. By combining data of the pixels 201, a radiation image is obtained.

Next, the offset image obtaining sequence will be described. The offset image obtaining sequence includes a resetting operation, an accumulating operation, and a reading operation. The control circuit 112 first performs the resetting operation once similarly to the waiting sequence. By this, a state of the pixel array 200 becomes a state obtained before start of the radiation image obtaining sequence. Thereafter, the control circuit 112 performs the accumulating operation and the reading operation similarly to the radiation image obtaining sequence so as to obtain an offset image. The offset image is also transferred from the radiation imaging apparatus 110 to the computer 120 similarly to the radiation image. When the offset image is subtracted from the radiation image, an offset component generated by the dark charge generated in the conversion elements C during the emission of a radial ray is removed from the radiation image.

In the reading operation described above, sensitivity of the pixels 201 may be changed. For example, when an On signal is supplied to the driving line Vg2, the switch elements S11 and S22 are turned on. In this case, a portion of the charge obtained by the conversion element C11 is transferred to the conversion element C12, and therefore, a potential of the signal line Sig1 is changed due to a capacitance generated between the source and the drain of the switch element S12. As a result, the number of signals read by the signal line Sig1 is larger than that obtained by the conversion element C22.

Furthermore, in the second partial reading operation, the charge obtained by the conversion element C11 is transferred to the signal line Sig1 through the two switch elements S11 and S12, for example. Therefore, a portion of the charge obtained by the conversion element C11 is not transferred and remains, and sensitivity of the pixel 201 including the conversion element C11 may be degraded.

To reduce the change of the sensitivity of the pixel 201 described above, the radiation imaging apparatus 110 may divide an image captured in a state in which a subject exists by an image captured in a state in which a subject does not exist and perform gain correction on a resultant image. Alternatively, the radiation imaging apparatus 110 may calculate a ratio of sensitivity of the first partial reading operation to sensitivity of the second partial reading operation in advance so as to correct pixel values using the sensitivity ratio. Furthermore, the conversion elements C of the pixels 201 in the odd-numbered columns and the conversion elements C of the pixels 201 in the even-numbered columns may have different aperture rates. Alternatively, the switch elements S of the pixels 201 in the odd-numbered columns and the switch elements S of the pixels 201 in the even-numbered columns may have different on-resistances.

When the first partial reading operation and the second partial reading operation are performed for each pixel column, stripes may appear on an image due to a difference between sensitivity characteristics and a difference between dark characteristics. Therefore, the pixels 201 from which signals are read in the first partial reading operation are arranged in a checkered pattern (in this case, the pixels 201 from which signals are read in the second partial reading operation are also arranged in a checkered pattern) so that the stripes are difficult to be seen in the image.

As with the reading operation described above, the reading is performed on the entire pixel array 200 after the pixel array 200 is divided into two in terms of time, and therefore, a noise component externally mixed into the radiation imaging apparatus 110 hardly appears in an image. Furthermore, when the image obtained by the first partial reading operation is used as a preview image, an engineer may immediately check a captured image after emission of a radial ray.

A length of the signal line Sig in the pixel array 200 is changed depending on a position of a connection of the reading circuit 220 in the pixel array 200. The signal line Sig generates thermal noise depending on a line length, and the shorter the signal line Sig is, the smaller the noise is. A random noise of a region of interest may be reduced by arranging a short signal line Sig in a center portion of the pixel array 200 which is the region of interest.

In the operation example described above, the second partial reading operation is different from the first partial reading operation. Alternatively, the second partial reading operation may be the same as the first partial reading operation. Specifically, in the second partial reading operation, the driving circuit 210 supplies an On signal only to the driving line Vg1. By this, the switch element S12 is turned on and the conversion element C12 and the signal line Sig1 are brought into a conductive state. At a time point when the second partial reading operation is started, the charge obtained by the conversion element C12 has been read, and a portion of the charge obtained by the conversion element C11 has been transferred to the conversion element C12. Accordingly, in a case where the On signal is supplied only to the driving line Vg1, a portion of the charge transferred to the conversion element C12 is read to the signal line Sig1. An amount of the read charge is a value obtained by multiplying an amount of the charge obtained by the conversion element C11 by a capacitance ratio of the conversion element C11 to the conversion element C12. For example, in a case where capacitances of the conversion element C11 and the conversion element C12 are equal to each other, a half of the charge obtained by the conversion element C11 is read to the signal line Sig1. Thereafter, the radiation imaging apparatus 110 may calculate a signal value of the pixel 201 including the conversion element C11 by doubling the read signal. Alternatively, the radiation imaging apparatus 110 may generate an image obtained by enlarging a dynamic range by using the read signal as it is.

Second Embodiment

Figure 5:
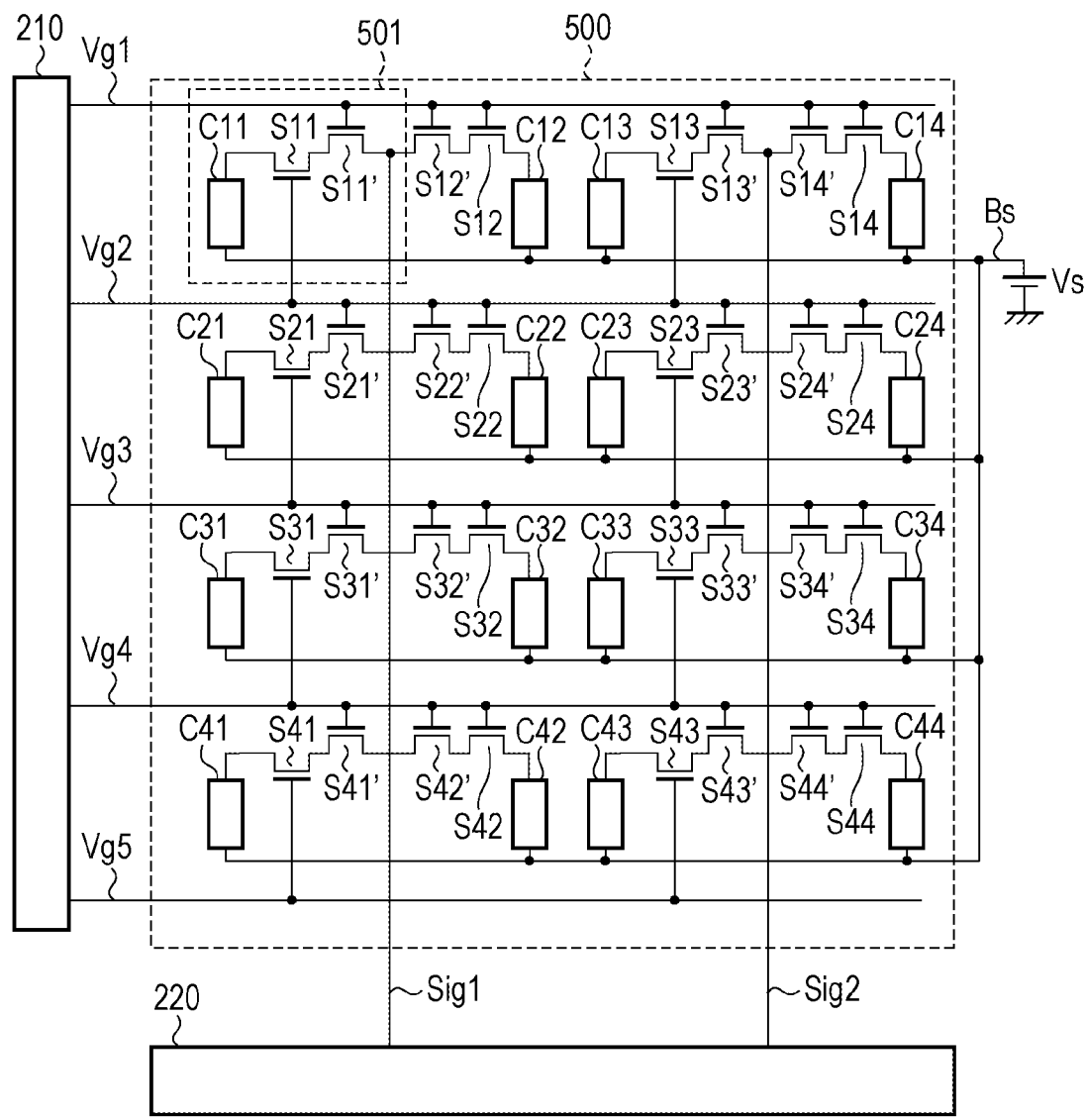
FIG. 5 is a diagram illustrating an example of a configuration of a radiation imaging apparatus according to a second embodiment of the present invention.
Figure 6:
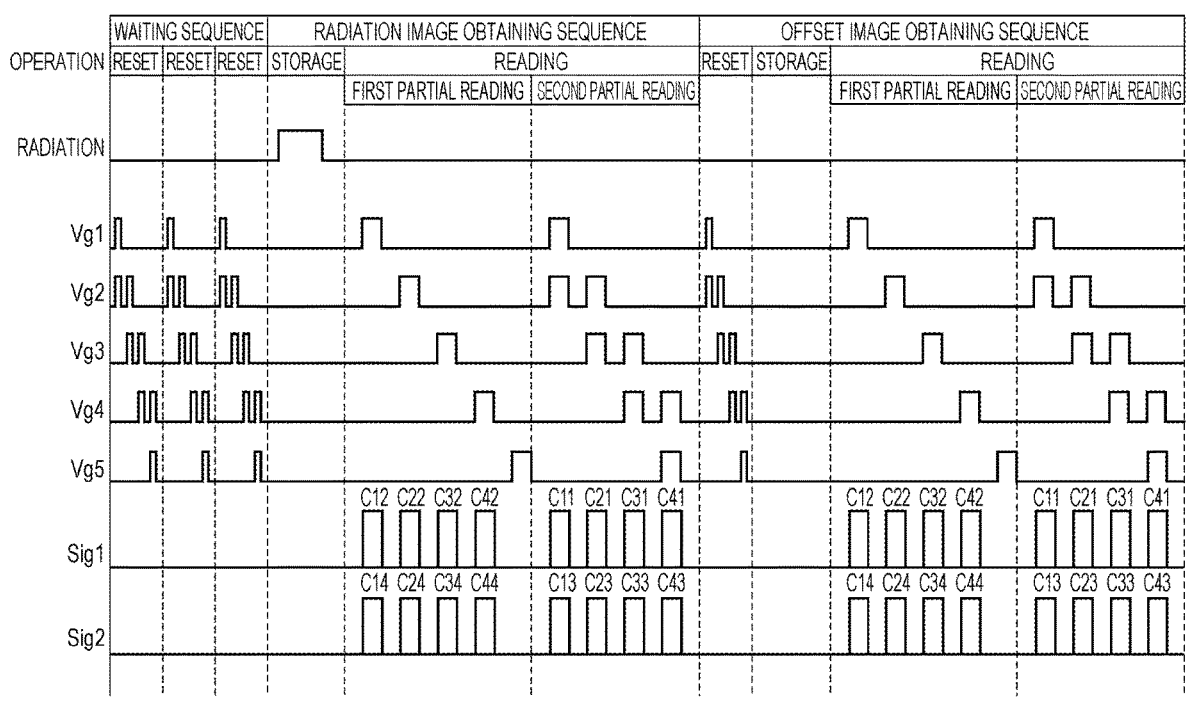
FIG. 6 is a diagram illustrating an example of an operation of a radiation imaging system according to the second embodiment of the present invention.

A radiation imaging system according to a second embodiment of the present invention will be described with reference to FIGS. 5 and 6. The radiation imaging system according to the second embodiment is different from the radiation imaging system 100 of the first embodiment in that a radiation imaging apparatus 110 includes a pixel array 500 illustrated in FIG. 5 instead of the pixel array 200 illustrated in FIG. 2, and other portions may be the same as those of the radiation imaging system 100 of the first embodiment. Therefore, descriptions which may be the same as those of the first embodiment are omitted hereinafter.

The pixel array 500 includes, for example, a plurality of pixels 501 arranged in an array, a plurality of driving lines Vg1 to Vg5, a plurality of signal lines Sig1 and Sig2, and a bias line Bs. The pixel array 500 includes a plurality of conversion elements C11 to C44 and a plurality of switch elements S11 to S44 and S11' to S44'. In the description below, the conversion elements C11 to C14 are collectively referred to as a conversion element C, and switch elements S11 to S44 and S11' to S44' are collectively referred to as a switch element S. Each of the pixels 501 is configured by a combination of a single conversion element C and a pair of switch elements S. For example, the pixel 501 in a first row and a second column is configured by a combination of a conversion element C12 and switch elements S12 and C12'.

In each of the pixels 501 in the first row and even-numbered columns, control terminals of the two switch elements S are connected to the driving line Vg1. In each of the pixels 501 in the first row and odd-numbered columns, a control terminal of one of the pair of switch elements S is connected to the driving line Vg1 and a control terminal of the other of the pair of switch elements S is connected to the driving line Vg2. The same is true of the second to fourth rows. Furthermore, the conversion elements C of the individual pixels 501 are connected to the signal line Sig through the pairs of switch elements S which are directly connected to each other.

For example, the switch elements S11 and S11' are connected in series between the conversion element C11 and the signal line Sig1. The switch element S11 is connected to the signal line Sig1 through the switch element S11'. The switch elements S12 and S12' are connected in series between the conversion element C12 and the signal line Sig1. The switch elements S22 and S22' are connected in series between the conversion element C22 and the signal line Sig1. The conversion elements C12 and C22 are arranged in a direction in which the signal line Sig1 extends. The conversion elements C11 and C12 are arranged in a direction in which the driving line Vg1 extends.

In this connection form, the number of signal lines Sig may be a half of the number of columns in the pixel array 500. Furthermore, the number of driving lines Vg is larger by one than the number of rows in the pixel array 500. Therefore, when compared with a radiation detection panel which has driving lines for individual pixel rows and signal lines for individual pixel columns, the number of contacts between the pixel array 500 and peripheral circuits (a driving circuit 210 and a reading circuit 220) (the total number of the driving lines Vg and the signal lines Sig) is reduced. Consequently, configurations of the peripheral circuits are simplified.

A reading operation according to the second embodiment will be described in detail with reference to FIG. 6. Although charge read through the signal line Sig1 is mainly described hereinafter, the same is true of charge read through the signal line Sig2. First, the driving circuit 210 supplies an On signal only to the driving line Vg1. By this, the switch elements S12 and S12' are turned on and the conversion element C12 and the signal line Sig1 are brought into a conductive state, and therefore, charge obtained by the conversion element C12 is read to the signal line Sig1. On the other hand, since an Off signal is supplied to the driving line Vg2, the switch element S11 is in an Off state and the conversion element C11 and the signal line Sig1 are in a non-conductive state.

Accordingly, charge obtained by the conversion element C11 is not read to the signal line Sig1 at this time point.

After the charge obtained by the conversion element C12 is read, the driving circuit 210 supplies an On signal only to the driving line Vg2. By this, the switch elements S22 and S22' are turned on and the conversion element C22 and the signal line Sig1 are brought into a conductive state, and therefore, charge obtained by the conversion element C22 is read to the signal line Sig1. Although the switch element S11 is turned on, the conversion element C11 and the signal line Sig1 are in a non-conductive state since the switch element S11' is in an Off state. Furthermore, since the conversion element C11 is not connected to another conversion element through the switch element S11, the charge of the conversion element C11 is not transferred. After the charge obtained by the conversion element C22 is read, the driving circuit 210 sequentially supplies an On signal to the driving lines Vg3 to Vg5. Accordingly, charge obtained by the conversion elements C32 and C42 is similarly read to the signal line Sig1. A first partial reading operation is thus terminated.

Subsequently, a control circuit 112 performs a second partial reading operation. In the second partial reading operation, as with the first partial reading operation, charge is successively read from the pixels 201 in the first row to the pixels 201 in the last row (the fourth row). First, the driving circuit 210 supplies an On signal to the driving lines Vg1 and Vg2. By this, the switch elements S11, S11', S12, and S12' are turned on and the conversion element C11 and the signal line Sig1 are brought into a conductive state, and therefore, the charge obtained by the conversion element C11 is read to the signal line Sig1. The charge obtained by the conversion element C12 has been read by the first partial reading operation, and therefore, only the charge obtained by the conversion element C11 is read. Since the On signal is supplied to the driving line Vg2, the switch element S21' is also turned on. However, the switch element S21 is in an Off state, and therefore, charge obtained by the conversion element C21 is not read to the signal line Sig1.

After the charge obtained by the conversion element C11 is read, the driving circuit 210 successively supplies an On signal to the driving lines Vg2 to Vg5 in a unit of two lines. By this, the charge obtained by the conversion elements C21, C31, and C41 is similarly read to the signal line Sig1. The second partial reading operation is thus terminated.

In the second embodiment, since scanning directions of the driving line Vg in the first partial reading operation and the second partial reading operation are the same, the control of the driving circuit 210 may be simplified.

Third Embodiment

Figure 7:
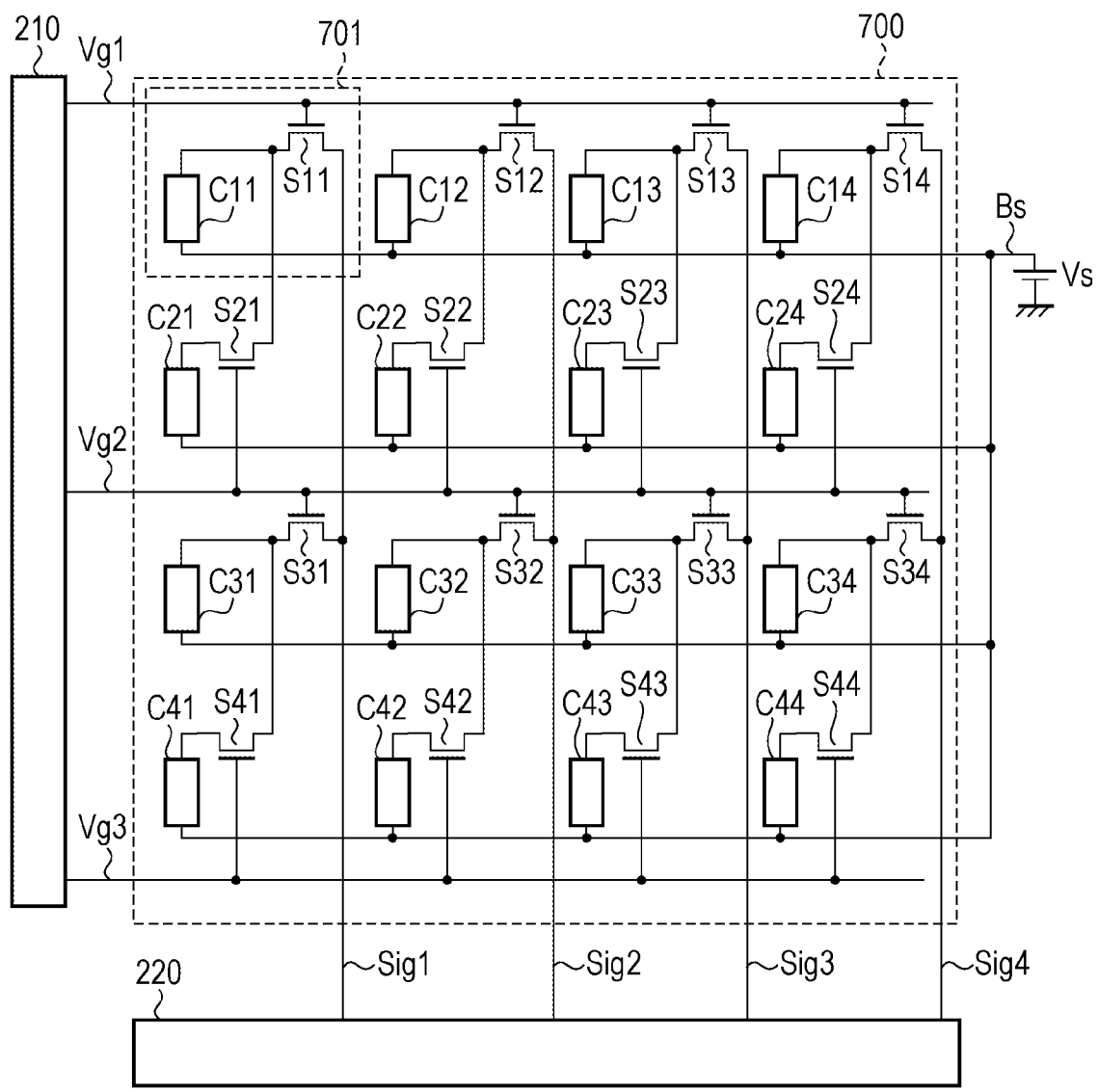
FIG. 7 is a diagram illustrating an example of a configuration of a radiation imaging apparatus according to a third embodiment of the present invention.
Figure 8:
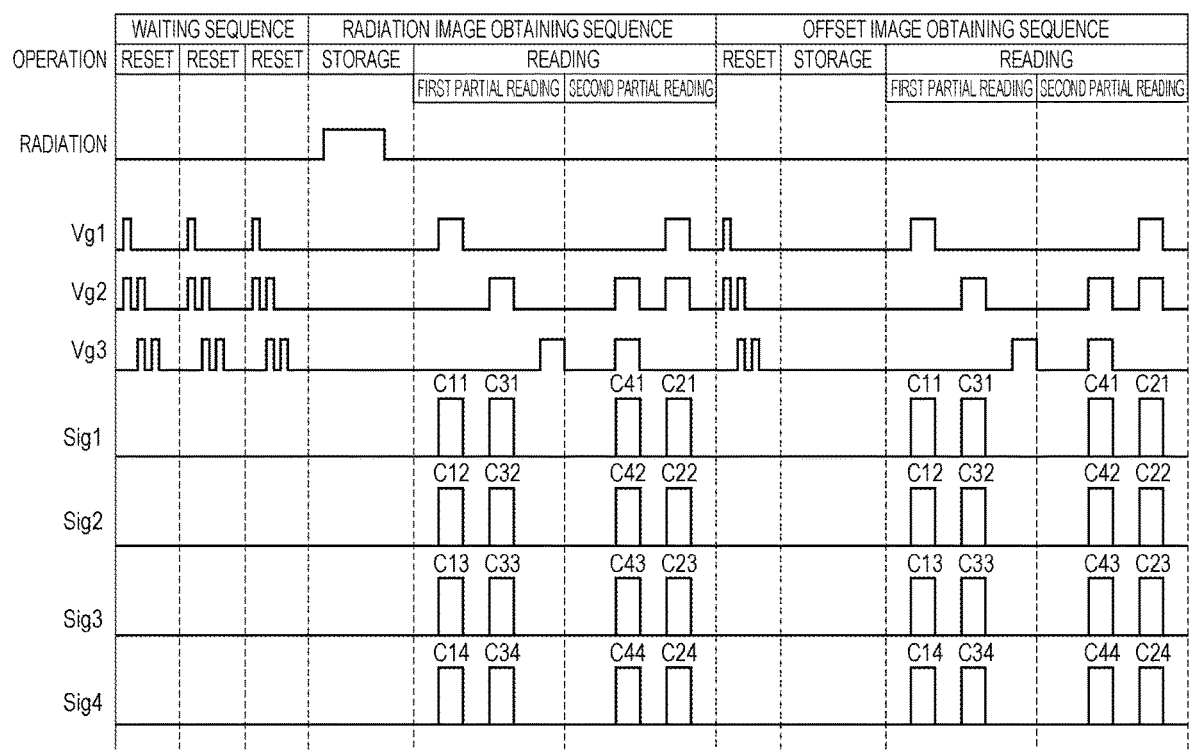
FIG. 8 is a diagram illustrating an example of an operation of a radiation imaging system according to the third embodiment of the present invention.

A radiation imaging system according to a third embodiment of the present invention will be described with reference to FIGS. 7 and 8. The radiation imaging system according to the third embodiment is different from the radiation imaging system 100 of the first embodiment in that a radiation imaging apparatus 110 includes a pixel array 700 illustrated in FIG. 7 instead of the pixel array 200 illustrated in FIG. 2, and other portions may be the same as those of the radiation imaging system 100 of the first embodiment. Therefore, descriptions which may be the same as those of the first embodiment are omitted herein.

The pixel array 700 includes, for example, a plurality of pixels 701 arranged in an array, a plurality of driving lines Vg1 to Vg3, a plurality of signal lines Sig1 and Sig4, and a bias line Bs. The pixel array 700 includes a plurality of conversion elements C11 to C44 and a plurality of switch elements S11 to S44. In the description below, the conversion elements C11 to C44 are collectively referred to as a conversion element C, and the switch elements S11 to S44 are collectively referred to as a switch element S. Each of the pixels 701 is configured by a combination of a single conversion element C and a single switch element S. For example, the pixel 701 in a first row and a second column is configured by a combination of the conversion element C12 and the switch element S12.

Control terminals of the switch elements S of the pixels 701 in the first row are connected to the driving line Vg1. Control terminals of the switch elements S of the pixels 701 in a second row are connected to the driving line Vg2. Control terminals of the switch elements S of the pixels 701 in a third row are connected to the driving line Vg2. Control terminals of the switch elements S of the pixels 701 in a fourth row are connected to the driving line Vg3. Specifically, the conversion elements C of the pixels 701 in the odd-numbered rows are connected to the signal line Sig through the switch elements S included in the same pixels. The conversion elements C of the pixels 701 in the even-numbered rows are connected to the signal line Sig through the switch elements S included in the same pixels and the switch elements in the pixels disposed adjacent to the same pixels in a column direction (a direction in which the signal line Sig extends).

For example, the switch element S11 is connected between the conversion element C11 and the signal line Sig1. The switch elements S11 and S21 are connected in series between the conversion element C21 and the signal line Sig1. The switch element S21 is connected to the signal line Sig1 through the switch element S11. The switch element S31 is connected between the conversion element C31 and the signal line Sig1. The conversion elements C11, C21, and C31 are arranged in a direction in which the signal line Sig1 extends.

In this connection form, the number of driving lines Vg may be larger by one than a half of the number of rows of the pixel array 700. Furthermore, the number of signal lines Sig is the same as the number of columns of the pixel array 700. Therefore, when compared with a radiation detection panel which has driving lines for individual pixel rows and signal lines for individual pixel columns, the number of contacts between the pixel array 700 and peripheral circuits (a driving circuit 210 and a reading circuit 220) (the total number of the driving lines Vg and the signal lines Sig) is reduced. Consequently, configurations of the peripheral circuits are simplified.

A reading operation according to the third embodiment will be described in detail with reference to FIG. 8. Although charge read through the signal line Sig1 is mainly described, the same is true of charge read through the signal lines Sig2, Sig3, and Sig4. First, the driving circuit 210 supplies an On signal only to the driving line Vg1. By this, the switch element S11 is turned on and the conversion element C11 and the signal line Sig1 are brought into a conductive state, and therefore, charge obtained by the conversion element C11 is read to the signal line Sig1. On the other hand, since an Off signal is supplied to the driving line Vg2, the switch element S21 is in an Off state and the conversion element C21 and the signal line Sig1 are in a non-conductive state. Accordingly, the charge obtained by the conversion element C21 is not read to the signal line Sig1 at this time point.

After the charge obtained by the conversion element C11 is read, the driving circuit 210 supplies an On signal only to the driving line Vg2. By this, the switch element S31 is turned on and the conversion element C31 and the signal line Sig1 are brought into a conductive state, and therefore, charge obtained by the conversion element C31 is read to the signal line Sig1. Furthermore, the switch element S21 is also turned on, and therefore, the conversion element C11 and the conversion element C21 are brought into a conductive state through the switch element S21. Therefore, a portion of the charge obtained by the conversion element C21 is transferred to the conversion element C11. On the other hand, since an Off signal is supplied to the driving line Vg1, the switch element S11 is in an Off state and the conversion element C21 and the signal line Sig1 are in a non-conductive state. Accordingly, the charge obtained by the conversion element C21 is not read to the signal line Sig1 at this time point. After the charge obtained by the conversion element C31 is read, the driving circuit 210 supplies an On signal to the driving line Vg3. A first partial reading operation is thus terminated.

Subsequently, the control circuit 112 performs a second partial reading operation. In the second partial reading operation, contrary to the first partial reading operation, charge is read from the pixels 201 in the last row (the fourth row) to the pixels 201 in the first row. First, the driving circuit 210 supplies an On signal to the driving lines Vg2 and Vg3. By this, the switch elements S31 and S41 are turned on and the conversion element C41 and the signal line Sig1 are brought into a conductive state, and therefore, charge obtained by the conversion element C41 is read to the signal line Sig1. Although a portion of the charge obtained by the conversion element C41 is transferred to the conversion element C31 in the first partial reading operation, the portion of the charge is also read to the signal line Sig1 in addition to the charge obtained by the conversion element C41 since the conversion element C31 and the signal line Sig1 are in a conductive state. Furthermore, the charge obtained by the conversion element C31 has been read by the first partial reading operation, and therefore, only the charge obtained by the conversion element C41 is read. Since an On signal is supplied to the driving line Vg2, the switch element S21 is also turned on. However, since the switch element S11 is in an Off state, charge obtained by the conversion element C21 is not read to the signal line Sig1.

After the charge obtained by the conversion element C41 is read, the driving circuit 210 supplies an On signal to the driving lines Vg1 and Vg2. Accordingly, the charge obtained by the conversion elements C21 is similarly read to the signal line Sig1. The second partial reading operation is thus terminated.

According to the third embodiment, since the signal lines Sig are provided for individual pixel columns, an image may be read at higher speed when compared with the first embodiment.

Fourth Embodiment

Figure 9:
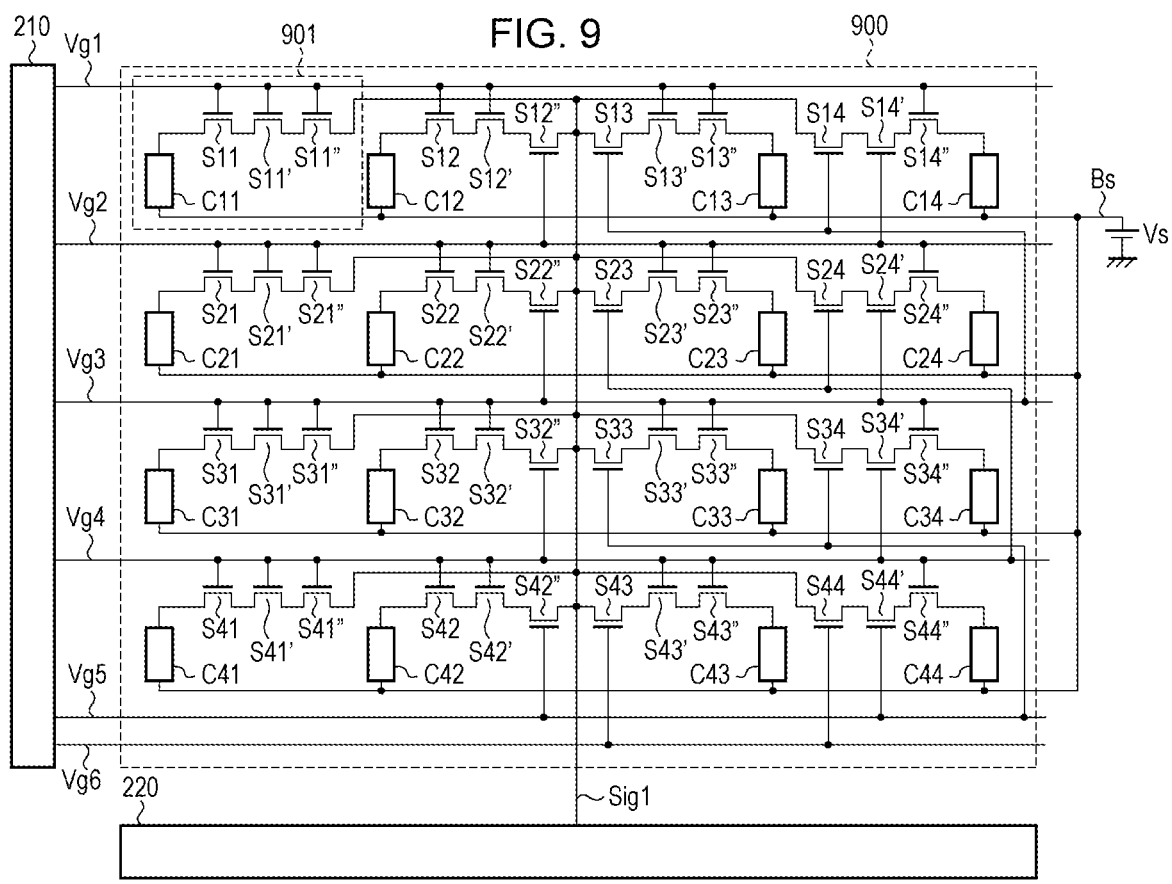
FIG. 9 is a diagram illustrating an example of a configuration of a radiation imaging apparatus according to a fourth embodiment of the present invention.
Figure 10:
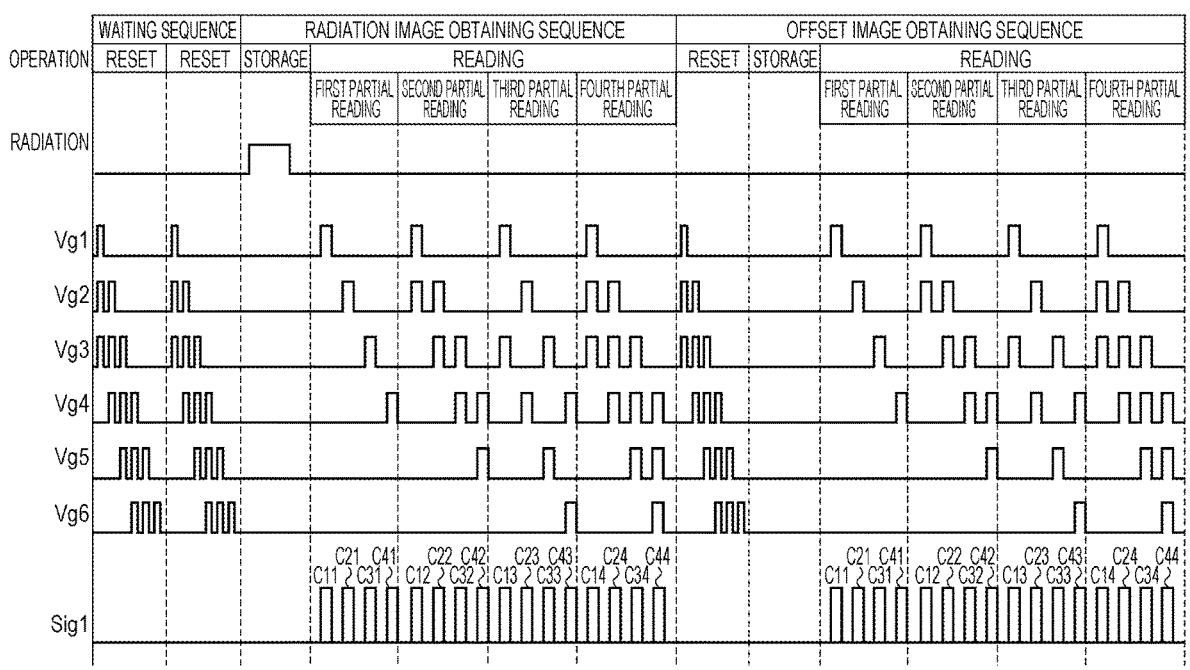
FIG. 10 is a diagram illustrating an example of an operation of a radiation imaging system according to the fourth embodiment of the present invention.

A radiation imaging system according to a fourth embodiment of the present invention will be described with reference to FIGS. 9 and 10. The radiation imaging system according to the fourth embodiment is different from the radiation imaging system 100 of the first embodiment in that a radiation imaging apparatus 110 includes a pixel array 900 illustrated in FIG. 9 instead of the pixel array 200 illustrated in FIG. 2, and other portions may be the same as those of the radiation imaging system 100 of the first embodiment. Therefore, descriptions which may be the same as those of the first embodiment are omitted herein.

The pixel array 900 includes, for example, a plurality of pixels 901 arranged in an array, a plurality of driving lines Vg1 to Vg6, a signal line Sig1, and a bias line Bs. The pixel array 900 includes a plurality of conversion elements C11 to C44 and a plurality of switch elements S11 to S44, S11' to S44', and S11" to S44". In the description below, the conversion elements C11 to C44 are collectively referred to as a conversion element C, and the switch elements S11 to S44, S11' to S44', and S11" to S44" are collectively referred to as a switch element S. The signal line Sig1 may be referred to as a signal line Sig. Each of the pixels 901 is configured by a combination of a single conversion element C and three switch elements S. For example, the pixel 201 in a first row and a second column is configured by a combination of the conversion element C12 and the switch elements S12, S12', and S12".

Control terminals of the three switch elements S of the pixel 901 in the first row and a first column are connected to the driving line Vg1. Control terminals of two of the three switch elements S in the first row and the second column are connected to the driving line Vg1 and a control terminal of the other of the switch elements S is connected to the driving line Vg2. Control terminals of two of the three switch elements S in the first row and a third column are connected to the driving line Vg1 and a control terminal of the other of the switch elements S is connected to the driving line Vg3. A control terminal of one of the three switch elements S of the pixel 901 in the first row and a fourth column are connected to the driving line Vg1, and a control terminal of one of the others of the switch elements S is connected to the driving line Vg2, and a control terminal of the remaining one of the switch elements S is connected to the driving line Vg3. The same is true of second to fourth rows. The configuration of the first to fourth rows may be repeated if the pixel array 900 includes pixels 901 in five columns or more. Specifically, the conversion element C of each of the individual pixels 901 is connected to the signal line Sig through the three switch elements S which are connected in series.

For example, the switch elements S11, S11', and S11" are connected in series between the conversion element C11 and the signal line Sig1. The switch elements S12, S12', and S12" are connected in series between the conversion element C12 and the signal line Sig1. The switch element S12 and S12' are connected to the signal line Sig1 through the switch element S12". The switch elements S13, S13', and S13" are connected in series between the conversion element C13 and the signal line Sig1. The switch element S13" and S13' are connected to the signal line Sig1 through the switch element S13. The switch elements S14, S14', and S14" are connected in series between the conversion element C14 and the signal line Sig1. The switch element S14" is connected to the signal line Sig1 through the switch element S14 and S14'. The switch elements S21, S21', and S21" are connected in series between the conversion element C21 and the signal line Sig1. The conversion elements C11 and C21 are arranged in a direction in which the signal line Sig1 extends. The conversion elements C11, C12, C13, and C14 are arranged in a direction in which the driving line Vg1 extends.

In this connection form, the number of signal lines Sig may be only a quarter of the number of columns of the pixel array 900. Furthermore, the number of driving lines Vg is larger by two than the number of rows of the pixel array 900. Therefore, when compared with the first embodiment, the number of contacts between the pixel array 900 and peripheral circuits (a driving circuit 210 and a reading circuit 220) (the total number of the driving lines Vg and the signal lines Sig) is reduced. Consequently, configurations of the peripheral circuits are further simplified.

A reading operation according to the fourth embodiment will be described in detail with reference to FIG. 10. In the fourth embodiment, a partial reading operation is performed four times. Although reading of electric signals from the pixels 901 in the first row is described hereinafter, the same is true of the pixels 901 in the other rows.

In a first partial reading operation, the driving circuit 210 supplies an On signal only to the driving line Vg1. By this, the switch element S11, S11', and S11" are turned on and the conversion element C11 and the signal line Sig1 are brought into a conductive state. Accordingly, charge is read from the conversion element C11 to the signal line Sig1. Here, since the switch elements S12", S13, S14, and S14' are in an Off state, charge obtained by the conversion elements C12, C13, and C14 is not read to the signal line Sig1. An Off signal is supplied to the driving line Vg1 in a process performed after the first partial reading operation, and therefore, the charge obtained by the conversion elements C12, C13, and C14 are not read to the signal line Sig1.

In a second partial reading operation, the driving circuit 210 supplies an On signal to the driving lines Vg1 and Vg2. By this, the switch element S12, S12', and S12" are turned on and the conversion element C12 and the signal line Sig1 are brought into a conductive state. Here, since the switch elements S13 and S14 are in an Off state, charge obtained by the conversion elements C13 and C14 is not read to the signal line Sig1. Furthermore, the charge obtained by the conversion element C11 has been read. An Off signal is supplied to the driving line Vg1 in a process performed after the second partial reading operation, and therefore, the charge obtained by the conversion elements C13 and C14 are not read to the signal line Sig1.

In a third partial reading operation, the driving circuit 210 supplies an On signal to the driving lines Vg1 and Vg3. By this, the switch element S13, S13', and S13" are turned on and the conversion element C13 and the signal line Sig1 are brought into a conductive state. Here, since the switch element S14' is in an Off state, the charge obtained by the conversion element C14 is not read to the signal line Sig1. Furthermore, the charge obtained by the conversion elements C11 and C12 has been read. An Off signal is supplied to the driving line Vg1 in a process performed after the third partial reading operation, and therefore, the charge obtained by the conversion element C14 is not read to the signal line Sig1.

In a fourth partial reading operation, the driving circuit 210 supplies an On signal to the driving lines Vg1, Vg2, and Vg3. By this, the switch element S14, S14', and S14" are turned on and the conversion element C14 and the signal line Sig1 are brought into a conductive state. The charge obtained by the conversion elements C11, C12, and C13 has been read.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A radiation imaging apparatus comprising:
   a plurality of conversion elements configured to convert a radial ray into an electric signal;
   a signal line configured to read electric signals obtained by the plurality of conversion elements;
   a plurality of switch elements configured to be connected between the plurality of conversion elements and the signal line; and
   a plurality of driving lines configured to be connected to control terminals of the plurality of switch elements,
   wherein the plurality of conversion elements include a first conversion element, a second conversion element, and a third conversion element,
   the plurality of driving lines include a first driving line and a second driving line,
   the first conversion element and the signal line are in a conductive state when a switch element connected to the first driving line is in an On state,
   the second conversion element and the signal line are in a conductive state when a switch element connected to the second driving line is in an On state, and
   the third conversion element and the signal line are in a conductive state when a switch element connected to the first driving line and a switch element connected to the second driving line are in an On state.

2. The radiation imaging apparatus according to claim 1, wherein the third conversion element and the signal line are in a non-conductive state when at least one of the switch element connected to the first driving line and the switch element connected to the second driving line is in an Off state.

3. The radiation imaging apparatus according to claim 1,
   wherein the plurality of switch elements include a first switch element connected between the first conversion element and the signal line and a second switch element connected between the third conversion element and the signal line,
   a control terminal of the first switch element is connected to the first driving line, and
   a control terminal of the second switch element is connected to the second driving line.

4. The radiation imaging apparatus according to claim 3, wherein the second switch element is connected to the signal line through the first switch element.

5. The radiation imaging apparatus according to claim 3,
   wherein the plurality of switch elements further include a third switch element,
   the second switch element is connected to the signal line through the third switch element, and
   a control terminal of the third switch element is connected to the first driving line.

6. The radiation imaging apparatus according to claim 1,
   wherein a first electric signal obtained by the first conversion element is read to the signal line by supplying an On signal to the first driving line and an Off signal to the second driving line,
   a third electric signal obtained by the second conversion element is read to the signal line by supplying an Off signal to the first driving line and an On signal to the second driving line after the first electric signal is read, and
   a second electric signal obtained by the third conversion element is read to the signal line by supplying an On signal to the first driving line and the second driving line after the third electric signal is read.

7. The radiation imaging apparatus according to claim 1,
   wherein a first electric signal obtained by the first conversion element is read to the signal line by supplying an On signal to the first driving line and an Off signal to the second driving line, a third electric signal obtained by the second conversion element is read to the signal line by supplying an Off signal to the first driving line and an On signal to the second driving line after the first electric signal is read, and a portion of a second electric signal obtained by the third conversion element which has been transmitted to the first conversion element is read to the signal line by supplying an On signal to the first driving line and an Off signal to the second driving line after the third electric signal is read.

8. The radiation imaging apparatus according to claim 1, wherein the first conversion element and the third conversion element are arranged in a direction in which the first driving line extends, and the first conversion element and the second conversion element are arranged in a direction in which the signal line extends.

9. The radiation imaging apparatus according to claim 1, wherein the first conversion element, the second conversion element, and the third conversion element are arranged in a direction in which the signal line extends.

10. The radiation imaging apparatus according to claim 1, wherein the plurality of conversion elements further include a fourth conversion element and a fifth conversion element, the plurality of driving lines further include a third driving line, the fourth conversion element and the signal line are in a conductive state when a switch element connected to the first driving line and a switch element connected to the third driving line are in an On state, and the fifth conversion element and the signal line are in a conductive state when a switch element connected to the first driving line, a switch element connected to the second driving line, and a switch element connected to the third driving line are in an On state.

11. A radiation imaging system comprising:

the radiation imaging apparatus according to claim 1; and signal processing means for processing a signal obtained by the radiation imaging apparatus.

* * * * *